(12) United States Patent
Mertens et al.

(10) Patent No.: US 6,773,688 B2
(45) Date of Patent: Aug. 10, 2004

(54) PROCESS FOR MANUFACTURE OF MOLECULAR SIEVES

(75) Inventors: Machteld Mertens, Boortmeerbeek (BE); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 81 days.

(21) Appl. No.: 09/997,778

(22) Filed: Nov. 29, 2001

(65) Prior Publication Data

US 2003/0100810 A1 May 29, 2003

(51) Int. Cl.$^7$ .............................................. C01B 37/08
(52) U.S. Cl. ................. 423/306; 423/DIG. 30
(58) Field of Search .......................... 423/306, DIG. 30

(56) References Cited

U.S. PATENT DOCUMENTS

| | | | |
|---|---|---|---|
| 4,440,871 A | | 4/1984 | Lok et al. .................... 502/234 |
| 4,898,722 A | | 2/1990 | Derouane et al. ........... 423/328 |
| 4,973,460 A | * | 11/1990 | Flanigen et al. ............. 423/705 |
| 5,126,308 A | * | 6/1992 | Barger et al. ................ 502/214 |
| 5,279,810 A | * | 1/1994 | Calabro ....................... 423/701 |
| 5,912,393 A | * | 6/1999 | Barger et al. ................ 585/640 |

FOREIGN PATENT DOCUMENTS

| | | | | |
|---|---|---|---|---|
| EP | 185525 A | | 6/1986 | ........... C01B/33/28 |
| EP | 541915 A | | 11/1991 | ........... C07C/11/02 |
| WO | WO 98/15496 | | 4/1998 | ........... C01B/25/45 |
| WO | WO 00/06493 | | 2/2000 | ........... C01B/37/04 |
| WO | WO 01/36328 | | 5/2001 | ........... C01B/37/06 |

OTHER PUBLICATIONS

Dahl et al., "The Effect of Crystallite Size on the Activity and Selectivity of the Reaction of Ethanol and 2-propanol over SAPO-34" *Microporous and Mesoporous Materials*, vol. 29 pp. 159–171, (1999).

* cited by examiner

*Primary Examiner*—David Sample
(74) *Attorney, Agent, or Firm*—Jaimes Sher

(57) ABSTRACT

Small particle size silicoaluminophosphate molecular sieves are obtained by providing the source of the silicon in the form of a basic organic solution.

43 Claims, No Drawings

PROCESS FOR MANUFACTURE OF MOLECULAR SIEVES

FIELD OF INVENTION

This invention relates to molecular sieves and processes for their manufacture. More especially it relates to a variation in the preparation of synthesis mixtures to control product characteristics. The invention relates primarily to the manufacture of phosphorus-containing molecular sieves, especially silicoaluminophosphates.

BACKGROUND OF THE INVENTION

In U.S. Pat. No. 4,440,871, the preparation of a number of phosphorus-containing molecular sieves is described.

The patent particularly describes processes for the manufacture of numerous crystalline microporous silicoaluminophosphates (SAPO's) including SAPO-34, employing sources of silicon (e.g., a silica sol), aluminium (e.g., hydrated aluminium oxide), and phosphorus (e.g., orthophosphoric acid), and an organic template, for example tetraethylammonium hydroxide (TEAOH), isopropylamine (iPrNH$_2$) or di-n-propylamine (DPA). The patent, the disclosure of which is incorporated by reference herein, gives X-ray diffraction data for the SAPO's and describes their utilities in catalysis and absorption.

International Application WO 00/06493 describes obtaining phosphorus-containing molecular sieves of lower particle size and narrower size distribution by agitation, e.g., stirring or tumbling.

EP-A-541 915 is concerned with the conversion of methanol to olefins (MTO), especially light (C$_2$ to C$_4$) olefins using an aluminophosphate crystalline molecular sieve catalyst. The specification describes the advantages of small particle size catalysts in MTO processes, and provides a process for facilitating the manufacture of a small particle size material by stirring the synthesis mixture, producing SAPO-34 of median particle diameters, expressed as a mass distribution, in the range of about 0.6 to 1.4 μm.

EP-A-185 525 describes a process in which SAPO-37 is manufactured using a two-phase synthesis mixture. In an example there are used an aqueous phase containing phosphoric acid, alumina, and tetraethyl and tetrapropyl ammonium hydroxides as organic templates, and an organic phase comprising tetraethyl orthosilicate in hexanol, a solvent immiscible with water. In a comparative example, the silicon source, silica (Hisil), is dispersed in the tetrapropylammonium hydroxide.

International Application WO 01/36328 describes a process in which a metalloaluminophosphate molecular sieve is manufactured using an aqueous synthesis mixture comprising a template, sources of the elements essential to the structure of the sieve and an organic solvent miscible with water, the purpose of the solvent being to solubilize the source of the metal in the aqueous synthesis mixture. When the metal is silicon, the source may be a tetraalkyl orthosilicate.

The present invention is based on the observation that if the silicon-providing component is dissolved in an organic base prior to its incorporation in the synthesis mixture the resulting silicoaluminophosphate molecular sieve has a particle size smaller than that obtained from an otherwise identical synthesis procedure in which the silicon-providing component is added directly or is merely dispersed in another component of the synthesis mixture.

SUMMARY OF THE INVENTION

The present invention accordingly provides a process for the manufacture of a silicoaluminophosphate crystalline molecular sieve which comprises providing sources of aluminium, of phosphorus and of silicon, the source of silicon being a solution of the silicon component in a water-miscible liquid organic base or in an aqueous solution of a solid organic base, forming a synthesis mixture from said sources and any other material necessary to form the molecular sieve, and treating the synthesis mixture for a period and at a temperature appropriate for the manufacture of the molecular sieve.

DETAILED DESCRIPTION OF THE INVENTION

Crystalline molecular sieves obtainable by the process of the invention include those of the LEV structure type, e.g., SAPO-35, and those of the CHA structure type, e.g., SAPO-34 and 47. An especially preferred silicoaluminophosphate is SAPO-34.

The invention also provides a crystalline silico aluminophosphate molecular sieve, especially SAPO-34, the mean particle size of the molecular sieve being at most 400 nm, advantageously at most 200 nm, preferably at most 100 nm, and most preferably at most 50 nm. The molecular sieve is advantageously one obtainable by, and preferably is obtained by, the process of the invention. The mean particle size is measured by inspection of scanning electron micrographs (SEM's), the largest dimension of each particle being taken.

The invention especially provides SAPO-34 the particle size of which is such that at least 50%, and preferably at least 90%, of the crystals by number are smaller than 100 nm. Preferably at least 50% of the crystals are smaller than 50 nm.

The components of the synthesis mixture used in the present invention are typically those known in the art or as described in the literature as suitable for the production of the molecular sieve, as are the conditions of the hydrothermal treatment, except for the dissolution of the silicon source in the organic base.

The liquid in which the silicon source is dissolved is conveniently a liquid organic base (which may be in admixture with water) or an aqueous solution of a normally solid organic base that is being used as a template in the synthesis of the crystalline molecular sieve. Other organic bases may be used, provided that they do not interfere with the structure directing properties of the organic base being used as template. Conveniently, any template that is difficulty soluble in water may be mixed with (if liquid) or dissolved in (if solid) the basic organic solvent. Heating may be necessary to effect solution of the silicon source.

Advantageously, all the silicon source is dissolved in the solvent.

Although the invention is not to be regarded as limited by any theory, it is believed that the reduction in product particle size achieved by the process of the invention may be attributable to the predissolution of the silicon source providing an increased number of nucleation sites from commencement of molecular sieve crystal formation in the synthesis mixture.

In general, the treatment of the synthesis mixture to yield the desired crystalline molecular sieve, usually termed hydrothermal treatment, is advantageously carried out under autogenous pressure, for example in an autoclave, for example a stainless steel autoclave which may, if desired, be preferably lined. The treatment may, for example, be carried out at a temperature within the range of from 50° C., advantageously from 90° C., especially 120° C., to 250° C., depending on the molecular sieve being made. The treatment may, for example, be carried out for a period within the range of from 1 to 200 hours, preferably up to 100 hours, again depending on the molecular sieve being formed. The procedure may include an ageing period, either at room temperature or, preferably, at a moderately elevated temperature, before the hydrothermal treatment at more elevated temperature. The latter may include a period of gradual or stepwise variation in temperature.

As source for the phosphorus in the synthesis mixture, there may be mentioned phosphoric acid, organic phosphates, e.g., triethylphosphate, and aluminophosphates.

As source for aluminium in the synthesis mixture there may be mentioned alumina hydrate, alumina, sodium aluminate, pseudoboehmite, organic aluminium sources, e.g., alkoxides, for example, aluminium isopropoxide, aluminium phosphate.

As source for silicon there may be mentioned fumed silica, e.g., that sold under the trade name Aerosil; an aqueous colloidal suspension of silica, e.g., that sold under the trade name Ludox AS40 or Ludox HS40; or organic silicon sources, e.g., a tetraalkyl orthosilicate, especially tetraethyl orthosilicate, although the invention is more especially of importance when the source of silicon is an inorganic source, it being understood that dissolution in the basic organic solvent may effect physical or chemical changes in the source as added.

In addition, the synthesis mixture will contain an organic structure-directing agent (template). In general, as indicated above, these compounds are generally organic bases, especially nitrogen-containing bases, more especially amines and quaternary ammonium compounds, used either singly or in mixtures.

As templates there may be mentioned, for example, tetraethyl ammonium compounds, cyclopentylamine, aminomethyl cyclohexane, piperidine, triethylamine, cyclohexylamine, trimethyl hydroxyethylamine, morpholine, dipropylamine (DPA), pyridine, isopropylamine and mixtures thereof. Preferred templates are triethylamine, cyclohexylamine, piperidine, pyridine, isopropylamine, tetraethyl ammonium compounds, dipropylamine, and mixtures thereof. The tetraethylammonium compounds include tetraethyl ammonium hydroxide (TEAOH), and tetraethyl ammonium phosphate, fluoride, bromide, chloride, and acetate. Preferred tetraethyl ammonium compounds are the hydroxide and the phosphate. The molecular sieve structure may be effectively controlled using combinations of templates.

In the manufacture of SAPO-34, it has proved advantageous to use a mixture of templates. For example, a suitable template mixture is TEAOH, which is readily soluble in water, and DPA, which dissolves in water with some difficulty.

The treatment may be carried out with the vessel static or, preferably, with stirring or with rotating the vessel about a horizontal axis (tumbling). If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

A synthesis mixture for producing SAPO-34 according to the invention advantageously has a molar composition within the following ranges:

| | |
|---|---|
| $P_2O_5:Al_2O_3$ | 0.6 to 1.2:1, preferably 0.65 to 0.91:1 |
| $SiO_2:Al_2O_3$ | 0.01 to 0.5:1, preferably 0.1 to 0.5:1 |
| $H_2O:Al_2O_3$ | 10 to 100:1 | together with an organic template, advantageously tetraethylammonium hydroxide (TEAOH), dipropylamine (DPA), isopropylamine or morpholine, or a mixture of two or more such templates, in a proportion appropriate to yield SAPO-34. A preferred template mixture comprises TEAOH and DPA.

The invention also provides the use of a silicon source in the form of the silicon component in a solution, advantageously a basic organic solution, in the hydrothermal synthesis of a crystalline silicoaluminophosphate molecular sieve to control the particle size of the product.

The invention further provides the products of the processes and of the uses of the earlier aspects of the invention. The products, if required after cation exchange and/or calcining, have utility as catalyst precursors, catalysts, and separation and absorption media. They are especially useful in numerous hydrocarbon conversions, separations and absorptions. They may be used alone, or in admixture with other molecular sieves, in particulate form, supported or unsupported, or in the form of a supported layer, for example in the form of a membrane, for example as described in International Application WO 94/25151. Hydrocarbon conversions include, for example, cracking, reforming, hydrofining, aromatization, oligomerisation, isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons, especially of methanol to olefins, especially light olefins. SAPO-34 produced by the process of the invention is especially suitable for this conversion.

Conversion of oxygenates may be carried out with the oxygenate, e.g., methanol, in the liquid or, preferably, the vapour phase, in batch or, preferably, continuous mode. When carried out in continuous mode, a weight hourly space velocity (WHSV), based on oxygenate, of advantageously 1 to 1000, preferably 1 to 100, hour$^{-1}$ may conveniently be used. An elevated temperature is generally required to obtain economic conversion rates, e.g., one between 300 and 600° C., preferably from 400 to 500° C., and more preferably about 450° C. The catalyst may be in a fixed bed, or a dynamic, e.g., fluidized or moving, bed.

The oxygenate feedstock may be mixed with a diluent, inert under the reaction conditions, e.g., argon, nitrogen, carbon dioxide, hydrogen, or steam. The concentration of methanol in the feedstream may vary widely, e.g., from 5 to 90 mole per cent of the feedstock. The pressure may vary within a wide range, e.g., from atmospheric to 500 kPa.

EXAMPLES

The following Examples, in which parts are by weight unless otherwise indicated, illustrate the invention. The source and purity of starting materials are those first given, unless indicated otherwise.

Example 1

This example illustrates the manufacture of SAPO-34 using the process of the invention.

A synthesis mixture was prepared from the following components in the proportions shown.

| Component | | Proportion |
|---|---|---|
| A | Colloidal silica (Ludox AS40) 40% in water | 10.49 |
|   | TEAOH, (Eastern Chemical) 35% in water | 97.88 |
| B | Al$_2$O$_3$ (Condea Pural SB) | 31.60 |
|   | water | 119.20 |
| C | H$_3$PO$_4$ (Acros), 85% in water | 53.33 |
| D | DPA (Fluka) | 37.50 |

To the colloidal silica was added the TEAOH dropwise while stirring in a stainless steel autoclave. The mixture was heated over 2 hours to 100° C., and maintained at that temperature for 12 hours, the resulting solution forming Component A.

Al$_2$O$_3$ was placed in the bowl of a Kenwood mixer, and water added with stirring to form a slurry of Component B. Component C was then added, followed by Component A, and then Component D. The molar composition of the mixture was:

Al$_2$O$_3$:P$_2$O$_5$:0.3SiO$_2$:TEAOH:1.59DPA:52H$_2$O

The synthesis mixture was heated in a stainless steel autoclave over 2 hours to 175° C. and maintained at that temperature without stirring for 96 hours. The solid product was recovered by centrifugation, washed four times with water to a conductivity of about 38 µS/cm and dried overnight at 120° C. XRD and SEM showed a pure SAPO-34 product with platelet crystals of uniform particle size; 50% by number of the crystals were smaller than 700 nm, 10% were larger than 1.2 µm. Yield 13.9% based on the weight of the original synthesis mixture.

By way of comparison, a synthesis mixture of the same molar composition was prepared, but the silica and the TEAOH were added separately to the mixture. Hydrothermal treatment produced a pure SAPO-34 with cube-like crystals of varied dimensions between 0.5 µm and 20 µm; 50% by number of the crystals were smaller than 1.6 µm, 10% were greater than 3.8 µm.

Example 2

Following the procedure of Example 1, a synthesis mixture was prepared having the following molar composition:

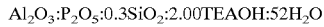
Al$_2$O$_3$:P$_2$O$_5$:0.3SiO$_2$:2.00TEAOH:52H$_2$O i.e., the colloidal silica, Ludox AS40, was dissolved over the course of 12 hours in the 35% TEAOH aqueous solution at 100° C., but the synthesis mixture contained only TEAOH, no DPA, as template.

The synthesis mixture was heated in a stainless steel autoclave over 2 hours to 175° C., and maintained at that temperature for 96 hours without stirring. The crystalline solid product was recovered by centrifugation, washed four times to a conductivity of about 32 µS/cm and dried overnight at 120° C. The crystals were pure SAPO-34; 50% of the crystals by number were smaller than 50 nm, 10% were larger than 100 nm.

A similar synthesis mixture was prepared, and subjected to hydrothermal treatment but this time with stirring, at 170 rpm, for a period of 48 hours only. The crystals after washing and drying as above were of particle size somewhat less than 0.1 µm.

Two comparison experiments were carried out, each using a synthesis mixture of the same molar composition but adding the silica and the TEAOH separately to the mixture, one carrying out the hydrothermal treatment on a static mixture, the other with stirring at 170 rpm.

The static mixture was heated over 2 hours to 175° C., and maintained at that temperature for 96 hours; the stirred mixture was also heated over 2 hours to 175° C. but maintained at that temperature for only 24 hours. In each case, the product was pure SAPO-34, of particle size about 1 µm.

Example 3

In this example, a synthesis mixture like that used in Example 1 was prepared, but only part of the silicon source was pre-dissolved. The H$_3$PO$_4$ was first added to the Al$_2$O$_3$/H$_2$O solution, followed by the addition of 96% of the silica, Ludox AS40, alone. Then the remainder of the Ludox AS40 was added, predissolved in the TEAOH (0.98 parts of Ludox AS140 in 223.43 parts TEAOH), followed by the DPA to give a synthesis mixture of molar composition:

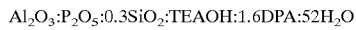
Al$_2$O$_3$:P$_2$O$_5$:0.3SiO$_2$:TEAOH:1.6DPA:52H$_2$O

The synthesis mixture was heated in a stainless steel autoclave over 8 hours to 175° C. and maintained at that temperature without stirring for 96 hours. The solid product was recovered as described in Example 1. Most of the crystals were between 1 and 2 µm, with some larger than 10 µm, i.e., the product has smaller particle size than if all the silica is added separately, but larger than that if all is predissolved.

In further comparative experiments premixing of silica (Ludox AS40) with TEAOH, at room temperature with and without aging, but without dissolution of the silica in the basic aqueous-organic solvent, gave slow crystallization, resulting in poor yields, together with amorphous material, and broad crystal size distribution.

What is claimed is:

1. A process for manufacturing a silicoaluminophosphate crystalline molecular sieve of pure LEV or CHA structure comprising particles having a mean particle size of at most 400 nm, the process comprising the steps of: (a) providing sources of aluminium, of phosphorus and of silicon, wherein the source of silicon is in solution with a water-miscible organic base; (b) forming a synthesis mixture from said sources; and (c) treating the synthesis mixture for a period of time and at a temperature sufficient to form the silicoaluminophosphate crystalline molecular sieve.

2. The process of claim 1, wherein the source of silicon is in solution in a water-miscible liquid organic base or an aqueous solution of a solid organic base.

3. The process of claim 2 wherein the water-miscible liquid organic base is in an admixture with water.

4. The process of claim 2 wherein the water-miscible liquid organic base functions as a structure-directing agent.

5. The process of claim 4 wherein the structure-directing agent is tetraethylammonium hydroxide (TEAOH).

6. The process of claim 4 wherein the structure-directing agent is a combination of tetraethylammonium hydroxide and dipropylamine.

7. The process of claim 1, wherein at least part of the process is carried out with agitation of the synthesis mixture.

8. The process of claim 1 wherein the silicoaluminophosphate crystalline molecular sieve is SAPO-34.

9. The process of claim 1 wherein the source of silicon comprises an inorganic silicon compound.

10. The process of claim 9 wherein the inorganic silicon compound is a colloidal silica.

11. The process of claim 1 wherein the silicoaluminophosphate crystalline molecular sieve is subjected to the step(s) of one or more of the group consisting of: washing, cation exchange and calcining.

12. A molecular sieve produced by the process of claim 1.

13. The process of claim 1, wherein the mean particle size is at most 200 nm.

14. The process of claim 13, wherein the mean particle size is at most 100 nm.

15. The process of claim 14, wherein the mean particle size is at most 50 nm.

16. The process of claim 1, wherein the silicoaluminophosphate molecular sieve comprises crystals, wherein at least 50% of the crystals by number are smaller than 100 nm.

17. The process of claim 16, wherein at least 50% of the crystals by number are smaller than 50 nm.

18. The process of claim 16, wherein at least 90% of the crystals by number are smaller than 100 nm.

19. A process for manufacturing a pure SAPO-34, the process comprising the steps of: (a) providing a source of aluminium and a source of phosphorus, (b) combining a source of silicon with a water-miscible liquid organic base or an aqueous solution of a solid organic base in an amount sufficient to form a SAPO-34 having a mean particle size of at most 400 nm; (c) forming a synthesis mixture from the combination of said sources in steps (a) and (b); and (d) subjecting the synthesis mixture to hydrothermal treatment.

20. A calcined crystalline silicoaluminophosphate molecular sieve comprising crystals, wherein at least 50% of the crystals by number are smaller than 100 nm.

21. The molecular sieve of claim 20, wherein at least 50% of the crystals by number are smaller than 50 nm.

22. The molecular sieve of claim 20, wherein at least 90% of the crystals by number are smaller than 100 nm.

23. A process for manufacturing a silicoaluminophosphate crystalline molecular sieve, the process comprising the steps of: (a) providing sources of aluminium. of phosphorus and of silicon, wherein the source of silicon is in solution with a water-miscible organic base; (b) forming a synthesis mixture from said sources; and (c) treating the synthesis mixture for a period of time and at a temperature sufficient to form the silicoaluminophosphate crystalline molecular sieve, wherein at least 50% of the silicoaluminophosphate crystalline molecular sieve particles are smaller than 100 nm.

24. The process of claim 23 wherein the water-miscible liquid organic base functions as a structure-directing agent.

25. The process of claim 24 wherein the structure-directing agent is tetraethylammonium hydroxide (TEAOH).

26. The process of claim 24 wherein the structure-directing agent is a combination of tetraethylammonium hydroxide and dipropylamine.

27. The process of claim 23, wherein at least part of the process is carried out with agitation of the synthesis mixture.

28. The process of claim 23, wherein the silicoaluminophosphate crystalline molecular sieve is SAPO-34.

29. The process of claim 23, wherein at least 50% of the particles by number are smaller than 50 nm.

30. The process of claim 23, wherein at least 90% of the crystals by number are smaller than 100 nm.

31. A process for manufacturing a silicoaluminophosphate crystalline molecular sieve, the process comprising the steps of: (a) dissolving a source of silicon by heating in a water-miscible organic base; (b) providing sources of aluminium and of phosphorus; (c) forming a synthesis mixture from said sources; and (d) treating the synthesis mixture for a period of time and at a temperature sufficient to form the silicoaluminophosphate crystalline molecular sieve.

32. The process of claim 31, wherein the water-miscible liquid organic base functions as a structure-directing agent.

33. The process of claim 32, wherein the structure-directing agent is tetraethylammonium hydroxide (TEAOH).

34. The process of claim 32, wherein the structure-directing agent is a combination of tetraethylammonium hydroxide and dipropylamine.

35. The process of claim 31, wherein at least part of the process is carried out with agitation of the synthesis mixture.

36. The process of claim 31, wherein the silicoaluminophosphate crystalline molecular sieve is SAPO-34.

37. The process of claim 31, wherein the silicoaluminophosphate crystalline molecular sieve comprises particles having a mean particle size of at most 400 nm.

38. The process of claim 37, wherein the mean particle size is at most 200 nm.

39. The process of claim 37, wherein the mean particle size is at most 100 nm.

40. The process of claim 37, wherein the mean particle size is at most 50 nm.

41. The process of claim 31, wherein the silicoaluminophosphate molecular sieve comprises crystals, wherein at least 50% of the crystals by number are smaller than 100 nm.

42. The process of claim 41, wherein at least 50% of the crystals by number are smaller than 50 nm.

43. The process of claim 41, wherein at least 90% of the crystals by number are smaller than 100 nm.

* * * * *